United States Patent [19]
Suk et al.

[11] Patent Number: 5,748,297
[45] Date of Patent: May 5, 1998

[54] ENDPOINT DETECTING APPARATUS IN A PLASMA ETCHING SYSTEM

[75] Inventors: Jong-Wook Suk; Jin-Ho Park; Shin-Hyun Park; Chang-Sik Kim, all of Suwon, Rep. of Korea

[73] Assignee: Samsung Electronics Co., Ltd., Rep. of Korea

[21] Appl. No.: 761,788

[22] Filed: Dec. 6, 1996

[30] Foreign Application Priority Data

Dec. 13, 1995 [KR] Rep. of Korea .................. 95-49160

[51] Int. Cl.$^6$ .................................................. G01N 21/62
[52] U.S. Cl. .......................... 356/72; 356/316; 156/626.1
[58] Field of Search .................................. 356/311, 316, 356/72; 156/626.1

[56] References Cited

U.S. PATENT DOCUMENTS 5,290,383  3/1994  Koshimizu ........................... 156/345

*Primary Examiner*—F. L. Evans
*Attorney, Agent, or Firm*—Jones & Volentine, LLP

[57] ABSTRACT

An apparatus used for detecting the endpoint or described completion point of an etching process has a detection window, an optical cable, and a bracket for fixedly holding the detection window and the optical cable with respect to each other. The detection window protrudes outwardly from a wall of a reaction chamber. The optical cable transmits light generated during an etching process from the detection window to a detecting device separate from the detection chamber. The bracket is attached to the wall of the reaction chamber so as to configure a space between the bracket and the detection window. The configuration reduces the intensity of the electric field formed between the bracket and plasma in the reaction chamber.

7 Claims, 3 Drawing Sheets

ENDPOINT DETECTING APPARATUS IN A PLASMA ETCHING SYSTEM

BACKGROUND OF THE INVENTION

1. Field of the Invention

The present invention relates to an apparatus for detecting the endpoint or desired completion point of a plasma etching system, and more particularly to a detecting apparatus capable of preventing adhesion of etching byproduct to a detection window in a plasma reaction chamber, so as to ensure reliability in detecting the endpoint or desired completion of the etching process.

2. Description of the Prior Art

In general, etching is a process for manufacturing semiconductor elements, in which thin films grown or deposited under a photoresist film are selectively eliminated after the development of the photoresist film. Etching may be classified into dry etching, as with plasma or laser, or wet etching, as with chemicals, such as photosensitive dielectrics or soluble polyimide precursors.

In plasma etching, a gas, such as fluoride including $CF_4$, along with a small amount of oxygen as an additive, is introduced into a reaction chamber previously in a vacuum state. High-frequency energy is applied between two electrodes so that a strong electric field is formed in the reaction chamber. The gas mixture is ionized into a plasma due to the electrical energy. In this state the gas is divided into active radicals F*, having high reactivity. The active radicals F* react with atoms such as silicon or their compounds included in the films to be etched, thereby yielding volatile compounds, such as $SiF_4$, to carry out the etching.

In both wet and dry etching processes, several factors play important roles in effecting the object of the process. These factors include control of the etch rate, control of the side etch, and durability of the photoresist. With all of these factors, the precise detection of the endpoint or desired completion of the etching process is most important. In this art the endpoint is defined as a desired completion point in the etching process for which the thin film of photoresist material has been completely eliminated. After etching, the underlying thin film or silicon substrate is entirely exposed in those areas where it has been previously covered by photoresist material. Consequently, the etching must end at this point before deteriorating the underlying thin films or silicon substrate.

Currently, several methods have been used in detecting the endpoint. For example, in wet etching, a generally used method for endpoint detection is to detect a change in the state or color of a thin film being etched. Another generally used method for endpoint detection is based on the comparison of the etch rate with the thickness of the thin film to be etched so as to predict the etch time.

With dry etching techniques, one method for endpoint detection is optically measuring a change in the refractive index of the thin film being etched. Another method of endpoint detection is to analyze the change in concentration of the active radicals. In yet another method, endpoint detection is accomplished by analyzing the byproducts generated during the etching process. In still another method, endpoint detection is carried out by monitoring a change in the impedance of the plasma.

FIG. 1 is a schematic diagram depicting a conventional endpoint detecting apparatus employed in an etching system. As shown, the conventional endpoint detecting apparatus includes a reaction chamber 1 kept in a vacuum state prior to introducing etching agents, a detection window 2 for transmitting light generated during the etching process, an optical cable 3, a bracket 4 for fixing the detection window in relation to the optical cable 3, and a detecting device 5 disposed away from the reaction chamber 1 for receiving light data via the optical cable.

The reaction chamber 1 accommodates the material to be processed, such as pieces of wafer (not shown). A reaction gas is introduced into the space between electrodes (not shown) in the reaction chamber and etching is performed by means of high-frequency energy applied via the electrodes. The detection window 2 is fitted in a side wall 1a of the reaction chamber and is formed from a plate made from transparent material such as quartz. The optical cable 3 is disposed near the detection window 2 and transmits the light generated during the etching process to the detecting device 5. The bracket 4 is attached to an outer surface of the side wall 1a of the reaction chamber 1 and fixedly supports the detection window 2 and the optical cable 3 with respect to each other. The detecting device 5 detects the endpoint by sensing the wavelength of the light generated during the process and transmitted from the detection window 2 through the optical cable 3.

In a conventional endpoint detecting apparatus, the light emitted from the plasma in the reaction chamber 1 is sensed through the transparent detection window 2. However, the further the etching proceeds, the more the detection window 2 becomes cloudy and the transmission of light through the detection window is diminished. This occurs because byproduct yielded in the reaction chamber during etching adheres to the side wall 1a or the detection window 2 due to its relatively low temperature in comparison with that of the plasma in the reaction chamber 1.

Further, the greater the number of pieces of the wafer to be etched, the lower the transmission of the light will be through the detection window 2 due to greater amount of debris. In particular, when the number of pieces of wafer supplied to be etched is not less than 2000, the amount of etching byproduct adhering to the detection window 2 is so great as to degrade or limit the transmission of light through the detection window 2. Thus, the intensity of the light transmitted to the optical cable 3 may be too low to obtain reliable detection of the endpoint. This is a major drawback of conventional etching systems.

To overcome this drawback, it is necessary to prevent or reduce the clouding of the detection window 2. One conventional endpoint detecting apparatus having an improved detection window 2 structure is depicted in FIG. 2. In this apparatus, the detection window 2 protrudes toward the bracket 4 from the side wall 1a and is in contact with the bracket 4. With such an arrangement, however, and disturbances in the plasma P flow occur and a more intense electric field is formed between the plasma P in the reaction chamber 1 and the bracket 4 because the bracket is grounded.

Also, since the aforementioned intensity of the electric field becomes larger as the distance between the bracket 4 and the plasma decreases, plasma spiking (shown as arrow P' in FIG. 3) occurs, and the plasma is further pulled toward the detection window 2. This further hinders transmission of the light generated in the reaction chamber 1 during the etching process. Therefore, the improved structure of FIGS. 2 and 3 do not have a substantial influence in preventing the adhesion of etching byproduct to the detection window.

SUMMARY OF THE INVENTION

It is an object of the present invention to provide an endpoint detecting apparatus in a plasma etching system, which can prevent adhesion of byproduct to a detection window.

Another object of the present invention is to provide an endpoint detecting apparatus arranged to prevent clouding of a detection window in a reaction chamber of the apparatus.

These and other objects of the present invention are achieved by an apparatus for detecting an endpoint in a plasma etching system having a plasma reaction chamber, where the apparatus includes a detection window provided on the wall of the reaction chamber and arranged so that this detection window protrudes outwardly from the reaction chamber wall. Also included is a detecting apparatus disposed separately from the reaction chamber and connected by an optical cable to the detection window. The light generated during the etching process is transmitted through the detection window via the optical cable to the detecting apparatus. Also included is a bracket for fixedly holding the detection window and the optical cable with respect to each other, the bracket being attached to an outer surface of the wall. The apparatus also includes an arrangement for reducing the intensity of an electric field formed between the bracket and the plasma in the reaction chamber.

BRIEF DESCRIPTION OF THE DRAWINGS

The above objects and advantages of the present invention will become more apparent by describing preferred embodiments thereof in detail while referring to the attached drawings, in which.

DETAILED DESCRIPTION OF THE PREFERRED EMBODIMENTS

Figure 4:
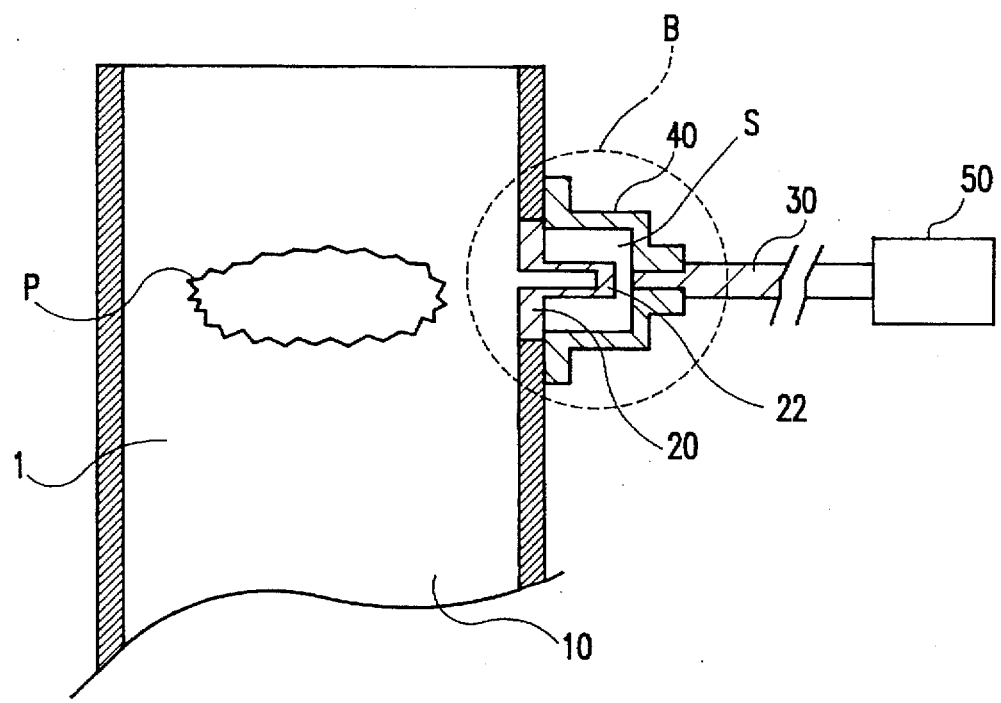
FIG. 4 is a longitudinal sectional schematic diagram of an endpoint detecting apparatus employed in an etching system according to the present invention.
Figure 5:
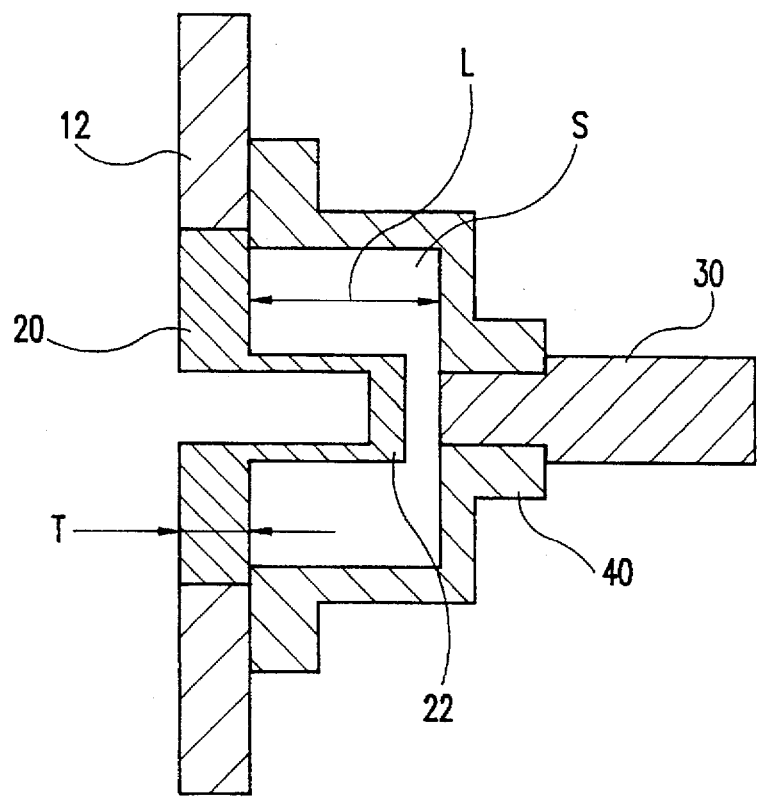
FIG. 5 is an enlarged sectional view of the elements encircled by the dashed line B in FIG. 4.

FIG. 4 is a longitudinal sectional schematic diagram of an endpoint detecting apparatus employed in an etching system according to the present invention, and FIG. 5 is an enlarged view of the elements encircled by dashed line B in FIG. 4.

The endpoint detecting apparatus according to the present invention includes a detection window 20, an optical cable 30, and a bracket 40. When the etching proceeds, pieces of wafer (not shown) which constitute the material to be processed are placed in a reaction chamber 10 and a reaction gas is introduced into the space between electrodes (not shown) in the reaction chamber 10. The etching is performed by the plasma P generated using high-frequency energy applied to the electrodes. The detection window 20 is fitted to a side wall 12 of the reaction chamber 10 and has a shape of a plate made from transparent material such as quartz. The detection window 20 protrudes outwardly from the side wall 12 of the reaction chamber 10 and transmits the light generated during the etching process. Optical cable 30 is disposed near the protrusion 22 of the detection window 20 and transmits the light generated during the etching process therethrough. A detecting device 50 is disposed separate from the reaction chamber 10. The detecting device 50 detects the endpoint by sensing the wavelength of the light generated during the process and transmitted from the detection window 20 through the optical cable 30.

Bracket 40 is attached (grounded) to an outer surface of the side wall 12 of the reaction chamber 10 and fixedly holds the detection window 20 and the optical cable 30 relative to each other. The bracket is spaced apart from the detection window 20 at a predetermined distance L, so that a certain space S is defined therebetween.

Figure 1:
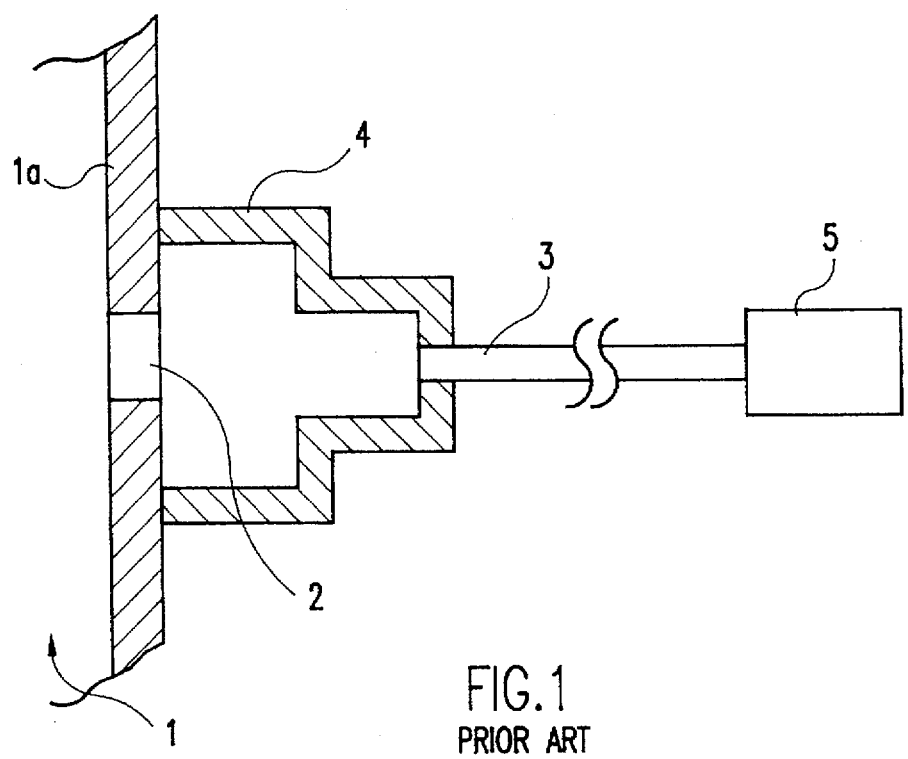
FIG. 1 is a longitudinal sectional schematic diagram of a conventional endpoint detecting apparatus in an etching system.
Figure 2:
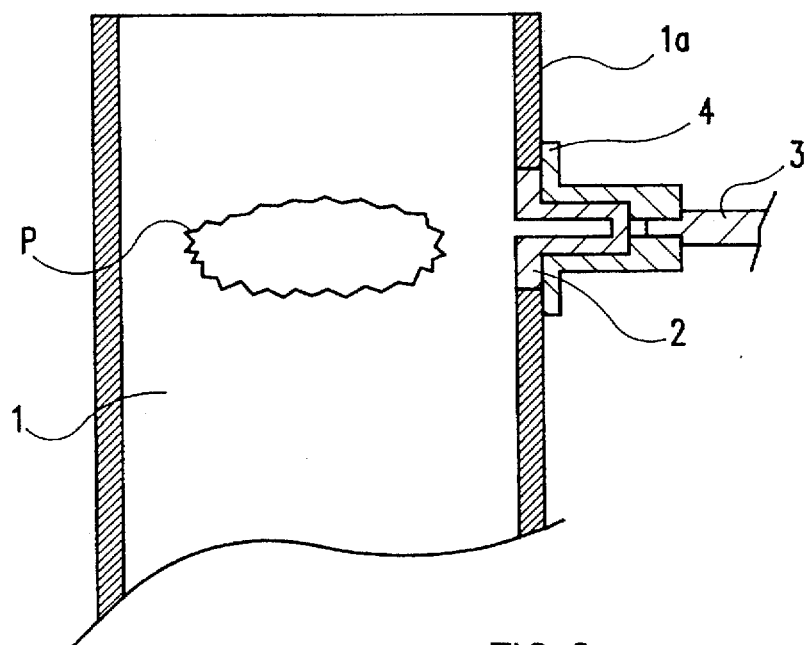
FIG. 2 is a longitudinal sectional schematic diagram of another conventional endpoint detecting apparatus in an etching system.
Figure 3:
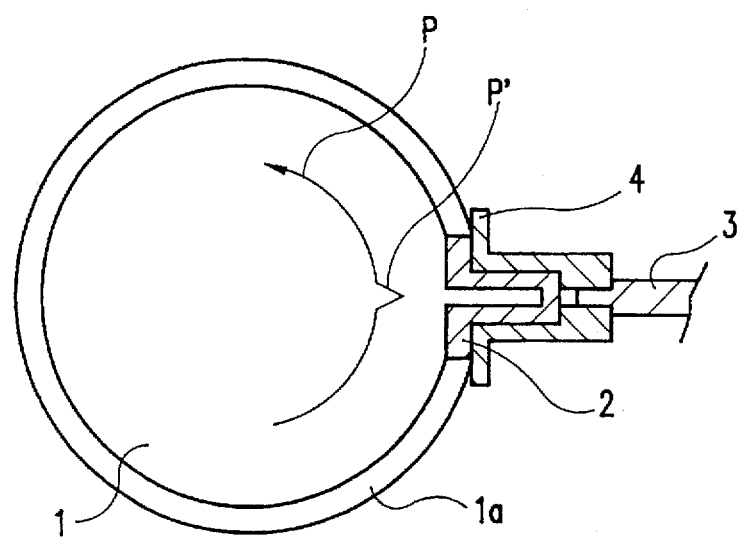
FIG. 3 is a transverse sectional diagram of the apparatus shown in FIG. 2, depicting the abnormal action of plasma in a conventional reaction chamber.
Figure 6:
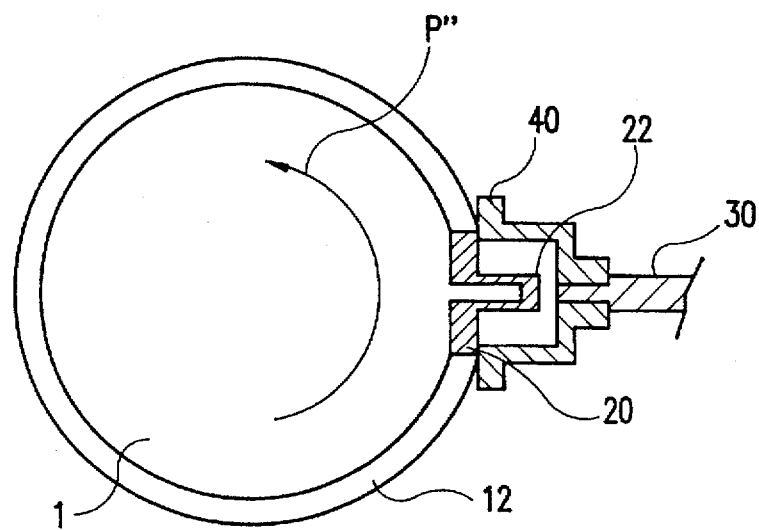
FIG. 6 is a transverse sectional diagram of the apparatus shown in FIG. 4, depicting a normal action of plasma in a reaction chamber.

The space S is defined for the purpose of reducing the intensity of the electric field formed between the plasma P in the reaction chamber 10 and the grounded bracket 40, thereby preventing the above-mentioned plasma spiking phenomenon P' (see FIG. 3) and maintaining a normal movement of the plasma in the reaction chamber 10 as shown by P" in FIG. 6.

It is preferred that the bracket 40 may be made from a material having low electric conductivity and high resistance because the intensity of the electric field between the plasma P in the reaction chamber 10 and the bracket 40 is reduced by such an arrangement. More preferably, the material may have a resistance above 0.01 ohm.

In order to further reduce the intensity of the electric field between the plasma P and the bracket 40, the distance L, defining the space S between the detection window 20 and the bracket 40, should be as large as possible. Preferably, the distance may be greater than or equal to 5 mm. The thickness T of the detection window 20 may be as large as possible in order to reduce the intensity of the electric field between the plasma P and the bracket 40 even when the bracket 40 is made from a material having a low resistance. Preferably, the thickness may be greater than or equal to 10 mm.

In the endpoint detecting apparatus according to the present invention, etching byproduct adherence to protrusion 22 of the detection window 20 is reduced and the detection window 20 is prevented from being clouded. Thus, the entire wavelength of light generated in the etching process is transmitted through the optical cable 30 to afford more precise detection of the endpoint. In addition, because the intensity of the electric field between the plasma P and the bracket 40 is substantially reduced, the action of the plasma can be maintained in a stable state thereby overcoming the shortcomings due to the outward protrusion of the detection window 20.

As a result, the present invention secures reliability in endpoint detection. The apparatus of the present invention has the further advantages in that stable action of the plasma may be maintained during the etching process in the apparatus, so that flaws in the manufacturing process are prevented. Consequently, the quality and the productivity of the apparatus are considerably improved.

While the present invention has been particularly shown and described with reference to the particular embodiments thereof, it will be understood by those skilled in the art that various changes in form and details may be effected therein without departing from the spirit and scope of the invention. Accordingly, the invention should be considered to include any and all configurations, modifications, variations, combinations, equivalent arrangements or expansions falling within the scope of the following claims.

What is claimed is:

1. A system for detecting an endpoint in a plasma etching system having a plasma reaction chamber, said system comprising:

a detection window provided at a wall of said reaction chamber, said detection window protruding outwardly from said reaction chamber wall;

a detecting apparatus disposed separately from said reaction chamber;

an optical cable for transmitting light to said detecting apparatus, said light being generated during an etching process and transmitted through said detection window to said optical cable;

a bracket for fixedly holding said detection window and said optical cable with respect to each other, said bracket being attached to an outer surface of said wall; and means, externally arranged to said reaction chamber, for reducing intensity of an electric field formed between the bracket and said reaction chamber.

2. The system of claim 1, wherein said means for reducing comprises a space defined between said bracket and said detection window.

3. The system as claimed in claim 1, wherein said bracket is made from a material having a high electrical resistance.

4. The system as claimed in claim 3, wherein said bracket has an electric resistance not less than 0.01 ohm.

5. The system as claimed in claim 2, wherein plasma in said reaction chamber is configured in a stable state.

6. The system as claimed in claim 2, wherein said bracket is spaced apart from said detection window at a distance not less than 5 mm.

7. The system as claimed in claim 4, wherein said bracket has a thickness not less than 10 mm.

* * * * *